US010993702B2

(12) United States Patent
Nagai et al.

(10) Patent No.: US 10,993,702 B2
(45) Date of Patent: May 4, 2021

(54) ULTRASONIC DIAGNOSTIC APPARATUS

(71) Applicant: TOSHIBA MEDICAL SYSTEMS CORPORATION, Otawara (JP)

(72) Inventors: Taketoshi Nagai, Nasushiobara (JP); Yasuhiro Takahashi, Nasushiobara (JP); Yuki Tamano, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 256 days.

(21) Appl. No.: 15/444,804

(22) Filed: Feb. 28, 2017

(65) Prior Publication Data

US 2017/0252012 A1 Sep. 7, 2017

(30) Foreign Application Priority Data

Mar. 3, 2016 (JP) .............................. JP2016-040906
Feb. 13, 2017 (JP) .............................. JP2017-023972

(51) Int. Cl.
*A61B 8/00* (2006.01)
*A61B 8/14* (2006.01)
(Continued)

(52) U.S. Cl.
CPC ................ *A61B 8/54* (2013.01); *A61B 8/145* (2013.01); *A61B 8/4488* (2013.01); *A61B 8/4494* (2013.01); *A61B 8/5207* (2013.01); *G01S 7/5202* (2013.01); *G01S 7/52096* (2013.01); *G01S 15/8915* (2013.01)

(58) Field of Classification Search
CPC ........... A61B 8/00; A61B 8/54; A61B 8/5207; A61B 8/145; A61B 8/4488; A61B 8/4494; G01S 7/52096; G01S 7/5202; G01S 15/8915
See application file for complete search history.

(56) References Cited

U.S. PATENT DOCUMENTS 5,113,706 A * 5/1992 Pittaro ................. A61B 8/4483
600/447
5,517,996 A 5/1996 Okada et al.
(Continued)

FOREIGN PATENT DOCUMENTS

JP 5-344970 A 12/1993
JP 7-265302 A 10/1995
(Continued)

OTHER PUBLICATIONS

Japanese to English Machine Translation of WO 2017/017801 (Year: 2019).*

(Continued)

*Primary Examiner* — Sanjay Cattungal
(74) *Attorney, Agent, or Firm* — Oblon, McClelland, Maier & Neustadt, L.L.P.

(57) ABSTRACT

In one embodiment, an ultrasonic diagnostic apparatus includes a plurality of transmission-wave generation circuits configured to supply a plurality of transducers of an ultrasonic probe with a plurality of transmission waves for driving the plurality of transducers via a plurality of channels; and a transmission control circuit configured to independently and dynamically control each of the plurality of transmission-wave generation circuits at a timing different for each channel.

8 Claims, 11 Drawing Sheets

(51) Int. Cl.
*G01S 7/52* (2006.01)
*A61B 8/08* (2006.01)
*G01S 15/89* (2006.01)

(56) References Cited

U.S. PATENT DOCUMENTS

| | | | | |
|---|---|---|---|---|
| 5,833,614 | A | * 11/1998 | Dodd | G01S 7/52038 |
| | | | | 600/447 |
| 5,897,501 | A | 4/1999 | Wildes et al. | |
| 6,193,659 | B1 | * 2/2001 | Ramamurthy | A61B 8/481 |
| | | | | 600/443 |
| 2003/0011285 | A1 | * 1/2003 | Ossmann | A61B 8/4281 |
| | | | | 310/334 |
| 2004/0158147 | A1 | * 8/2004 | Shifrin | G01S 7/5202 |
| | | | | 600/437 |
| 2009/0206676 | A1 | * 8/2009 | Chu | B06B 1/0215 |
| | | | | 307/106 |
| 2010/0298714 | A1 | * 11/2010 | Miyajima | A61B 8/06 |
| | | | | 600/459 |
| 2011/0012662 | A1 | * 1/2011 | Ma | G10K 11/346 |
| | | | | 327/295 |
| 2011/0270136 | A1 | * 11/2011 | Vitek | A61N 7/02 |
| | | | | 601/2 |
| 2012/0253198 | A1 | * 10/2012 | Hashiba | G01S 15/8925 |
| | | | | 600/447 |
| 2015/0031999 | A1 | * 1/2015 | Willsie | A61B 8/56 |
| | | | | 600/437 |

FOREIGN PATENT DOCUMENTS

| | | |
|---|---|---|
| JP | 8-628 A | 1/1996 |
| JP | 11-42225 A | 2/1999 |
| JP | WO 2005/016150 A1 | 10/2006 |
| JP | 2015-128532 A | 7/2015 |
| WO | WO-2017017801 A1 * 2/2017 | ............... A61B 8/00 |

OTHER PUBLICATIONS

Japanese Office Action dated Nov. 10, 2020 in Japanese Patent Application No. 2017-023972, 4 pages.

* cited by examiner

ULTRASONIC DIAGNOSTIC APPARATUS

CROSS-REFERENCE TO RELATED APPLICATION

This application is based upon and claims the benefit of priority from Japanese Patent Application No. 2016-040906, filed on Mar. 3, 2016, and Japanese Patent Application No. 2017-023972, filed on Feb. 13, 2017, the entire contents of each of which are incorporated herein by reference.

FIELD

Embodiments described herein relate generally to an ultrasonic diagnostic apparatus.

BACKGROUND

An ultrasonic diagnostic apparatus is configured to non-invasively acquire information inside an object by transmitting an ultrasonic pulse and/or an ultrasonic continuous wave generated by transducers included in an ultrasonic probe to an object's body, receiving a ultrasonic wave reflected due to difference in acoustic impedance between respective tissues in the object, and converting the reflected ultrasonic wave into an electric signal using the transducers.

In an ultrasonic examination using an ultrasonic diagnostic apparatus, various types of moving image data and/or real-time image data can be easily acquired by scanning an object such that an ultrasonic probe is brought into contact with a body surface of the object. Thus, an ultrasonic diagnostic apparatus is widely used for morphological diagnosis and functional diagnosis of an organ.

The number of transducers included in an ultrasonic probe tends to increase, although depending on a type of ultrasonic probe. In recent years, a two-dimensional array probe in which transducers are two-dimensionally arranged has been developed for acquiring three-dimensional data. A two-dimensional array probe has more transducers than a one-dimensional array probe.

The larger number of transducers of an ultrasonic probe becomes, the larger size of a transmission circuit configured to supply power to the respective transducers becomes, which increases power consumption of the transmission circuit. Additionally, a control signal and a clock signal are used in a transmission circuit for generating transmission waves. With an increase in number of transducers, a size of a circuit for distributing the control signal and the clock signal increases as well, and thus, noise caused by the control signal and the clock signal has also increased.

DETAILED DESCRIPTION

In one embodiment, an ultrasonic diagnostic apparatus includes a plurality of transmission-wave generation circuits configured to supply a plurality of transducers of an ultrasonic probe with a plurality of transmission waves for driving the plurality of transducers via a plurality of channels; and a transmission control circuit configured to independently and dynamically control each of the plurality of transmission-wave generation circuits at a timing different for each channel.

Hereinafter, embodiments of ultrasonic diagnostic apparatuses will be described with reference to the accompanying drawings.

First Embodiment (General Configuration)

Figure 1:
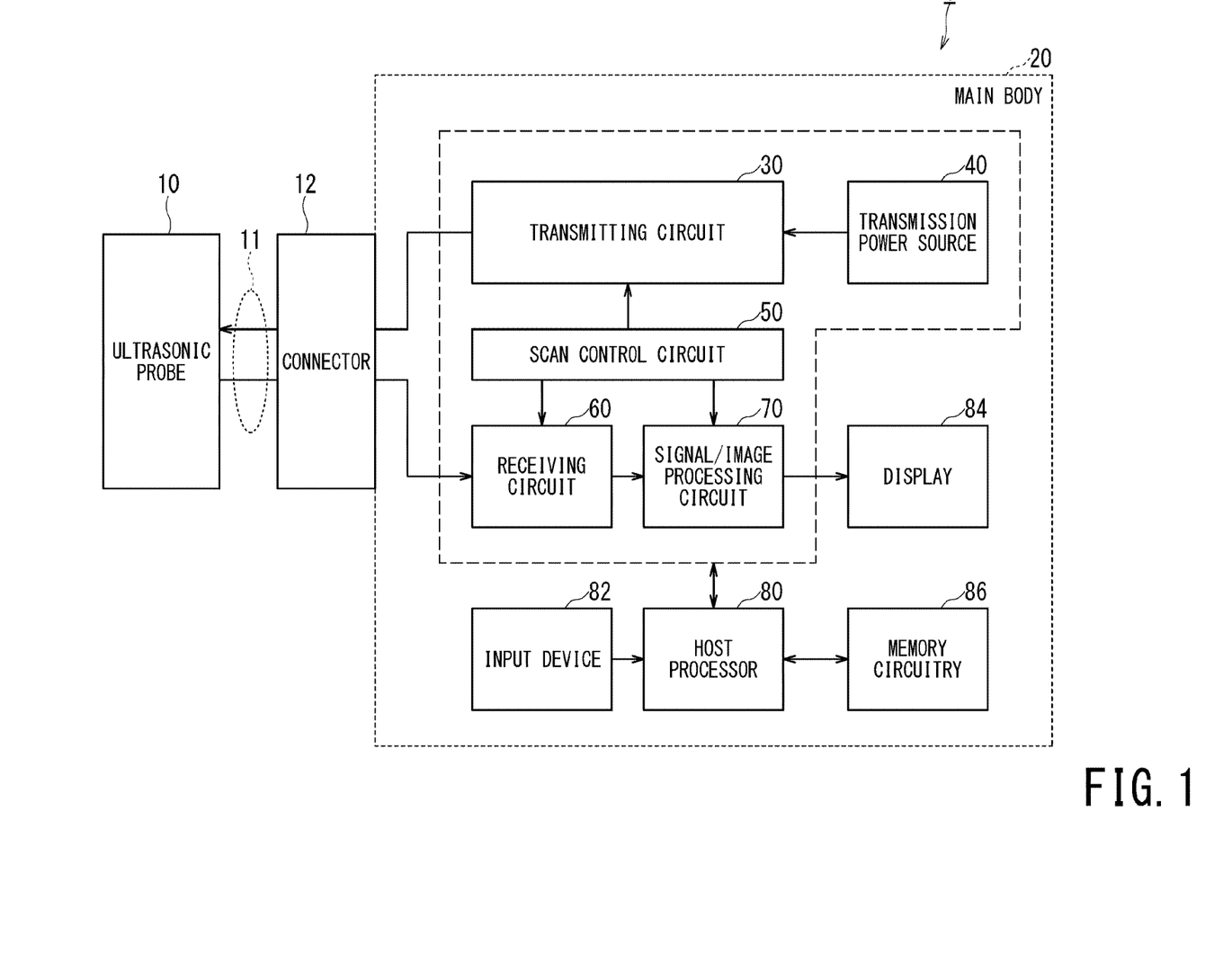
FIG. 1 is a block diagram illustrating general configuration of the ultrasonic diagnostic apparatus of the first embodiment.

FIG. 1 is a block diagram illustrating general configuration of an ultrasonic diagnostic apparatus 1 of the first embodiment. The ultrasonic diagnostic apparatus 1 includes an ultrasonic probe 10 and a main body 20.

Figure 2:
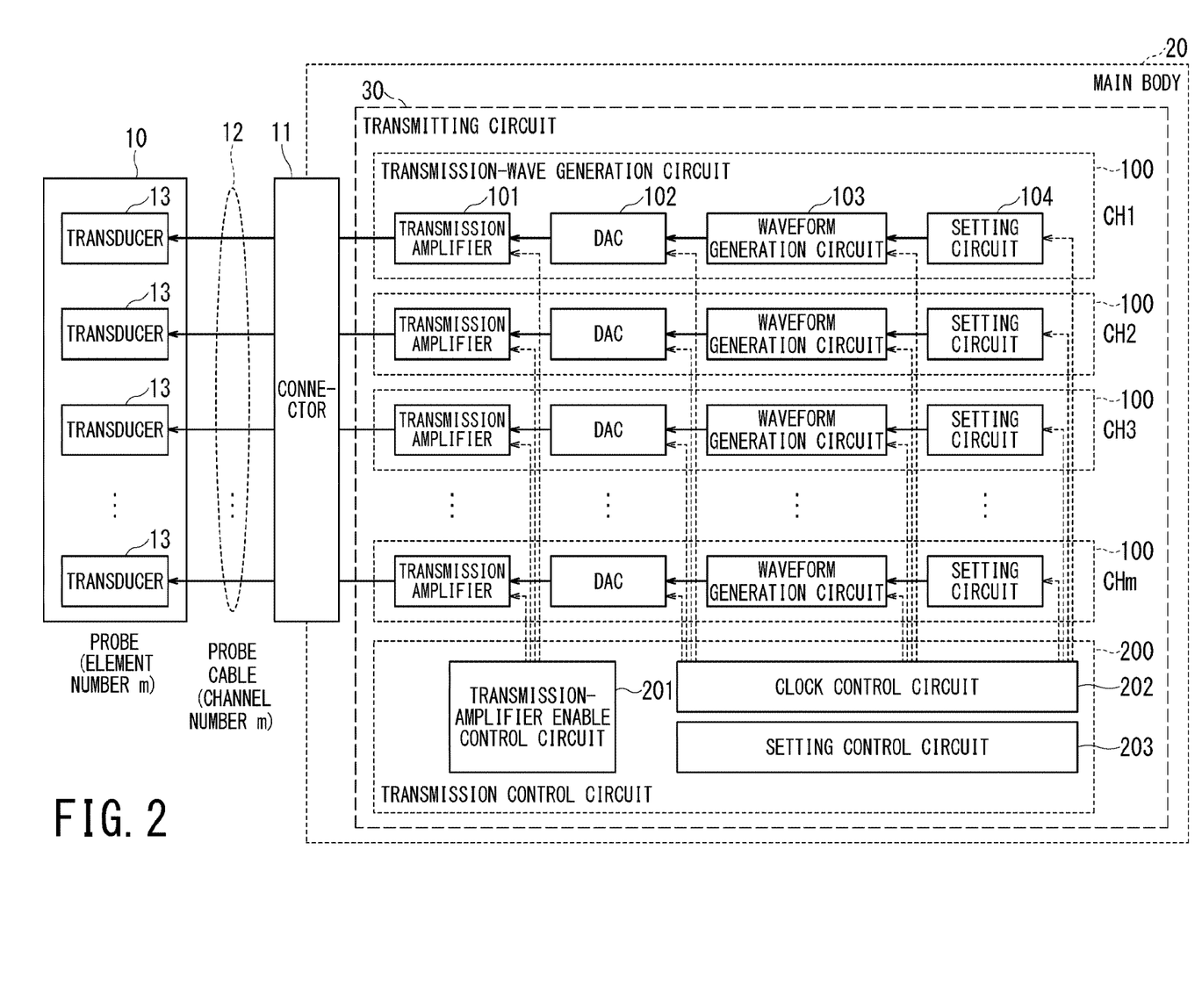
FIG. 2 is a block diagram illustrating detailed configuration of a transmitting circuit of the ultrasonic diagnostic apparatus of the first embodiment.

The ultrasonic probe 10 includes plural transducers 13 (FIG. 2). Each of the transducers 13 converts a transmission wave outputted as an electric signal from the main body 20 into an ultrasonic transmission wave, and applies the ultrasonic transmission wave to an object. Additionally, each of the transducers 13 converts an ultrasonic signal reflected from the object into a reception signal as an electric signal, and transmits the reception signal to the main body 20. The ultrasonic probe 10 is attachably/detachably connected to the main body via a probe cable 11 and a connector 12.

The ultrasonic probe 10 of the present embodiment may be a one-dimensional array probe in which the plural transducers 13 are linearly arrayed or may be a two-dimensional array probe in which the plural transducers 13 are two-dimensionally arrayed.

The main body 20 includes a transmitting circuit 30, a transmission power source 40, a scan control circuit 50, a receiving circuit 60, a signal/image processing circuit 70, a host processor 80, an input device 82, a display 84, and memory circuitry 86.

The transmitting circuit 30 generates a transmission wave, amplifies the transmission wave to a predetermined voltage, and then supplies the amplified transmission wave to the respective transducers 13 of the ultrasonic probe 10. Detailed configuration and operations of the transmitting circuit 30 will be described below.

The transmission power source 40 supplies the transmitting circuit 30 with electric power for generating transmission waves. The scan control circuit 50 outputs transmission/reception information to the transmitting circuit 30, the receiving circuit 60, and the signal/image processing circuit 70. The transmission/reception information includes, e.g., a scanning direction of an ultrasonic beam and a position of a focal point for scanning a predetermined range inside an object's body.

The receiving circuit 60 includes a preamplifier, analog-to-digital converter, a reception delay circuit, and an adder. The preamplifier amplifies reception signals outputted from the respective transducers 13 of the ultrasonic probe 10 to a predetermined voltage. The analog-to-digital converter converts the respective amplified reception signals into digital amounts (i.e., digital data). The reception delay circuit delays each of the digitized reception signals by a delay amount different for each transducer 13. The delay amounts are determined on the basis of information such as a scanning direction of a reception ultrasonic beam and a reception focal-point position, which are instructed by the scan control circuit 50. The adder performs phase-matching addition on the reception signals delayed by a delay amount different for each transducer 13.

Since a reception beam directed to a predetermined direction is formed by the reception delay circuit and the adder, the reception delay circuit and the adder are collectively referred to as a beam former in some cases. An output signal of the adder may be considered as a reception signal received by a formed reception beam.

The signal/image processing circuit 70 performs signal processing and image processing on reception signals outputted from the receiving circuit 60 according to its operation mode.

For instance, in a B-mode, the signal/image processing circuit 70 performs signal processing such as amplitude detection and logarithmic compression on the reception signals to acquire amplitude information of reflected waves. Additionally, for instance, in a color Doppler mode, the signal/image processing circuit 70 performs signal processing such as autocorrelation and MTI (Moving Target Indicator) filter processing on the reception signals to acquire power information and information on an average value and dispersion of blood flow velocity. Further, for instance, in a Doppler mode, the signal/image processing circuit 70 performs signal processing such as Fourier transform to acquire velocity information such as blood flow velocity in an instructed direction and at an instructed position.

Moreover, the signal/image processing circuit 70 performs scan conversion on the reception signals, which have been subjected to signal processing according to a beam direction and distance (depth), and then performs predetermined image processing on the reception signals to generate display data to be displayed on the display 84, i.e., an ultrasonic image.

The host processor 80 is equipped with electronic components such as a CPU, and controls an overall operation of the main body 20 by causing the CPU to execute predetermined programs stored in the memory circuitry 86. The input device 82 is, e.g., an operation device for a user such as a keyboard, a mouse, a joystick, and a trackball. When the display 84 is equipped with a touch panel, this touch panel is also included in the input device 82.

The display 84 is a display device configured of, e.g., a liquid crystal display. The display 84 displays various types of ultrasonic images generated by the signal/image processing circuit 70 in addition to data and information related to a user interface. The memory circuitry 86 stores various types of data and programs used by the main body 20.

(Configuration and Operation of Transmission Circuit)

Next, configuration and operations of the transmitting circuit 30 of the first embodiment will be described in detail.

FIG. 2 is a block diagram illustrating detailed configuration of the transmitting circuit 30 of the first embodiment. The transmitting circuit 30 supplies respective transmission waves to the plural transducers 13 of the ultrasonic probe 10 via plural channels.

The above-described "channel" means a path of transmission-wave generation included in the transmitting circuit 30, or a path of transmitting a transmission wave from the main body 20 to the ultrasonic probe 10. Thus, the number of transmission-wave generation circuits 100 included in the transmitting circuit 30 corresponds to the number of the channels.

Note that it is not necessarily required that the number of the channels matches the number of the transducers 13 of the ultrasonic probe 10 connected to the main body 20. For instance, when the number of the transducers is large like a 2D array probe, all the transducers may be grouped into plural subarrays, each of which is composed of a predetermined number of transducers, such that respective channels are assigned to the subarrays. In this case, the number of transducers is larger than channel number. Meanwhile, an ultrasonic probe 10 may be replaced by another prove via a connector. Thus, a probe having a smaller number of transducers than channel number is connected to the main body 20 in some cases. In the following, however, a description will be given of a case where channel number is equal to number of transducers, i.e., number of transducers is m and channel number is m (CH1 to CHm) as shown in FIG. 2.

Internal configuration of each of the transmission-wave generation circuits 100 is common to all the channels. Each of the transmission-wave generation circuits 100 includes a setting circuit 104, a waveform generation circuit 103, a digital-to-analog conversion circuit 102 (hereinafter, referred to as the DAC 102), and a transmission amplifier 101.

In order to control each of the above-described circuits 102, 103, 104, and the transmission amplifier 101, the transmitting circuit 30 is equipped with a transmission control circuit 200. The transmission control circuit 200 includes, as its internal configuration, a transmission-amplifier enable control circuit 201, a clock control circuit 202, and a setting control circuit 203.

Operations of the respective components inside the transmitting circuit 30 shown in FIG. 2 will be described with reference to FIG. 3 to FIG. 5.

Figure 3:
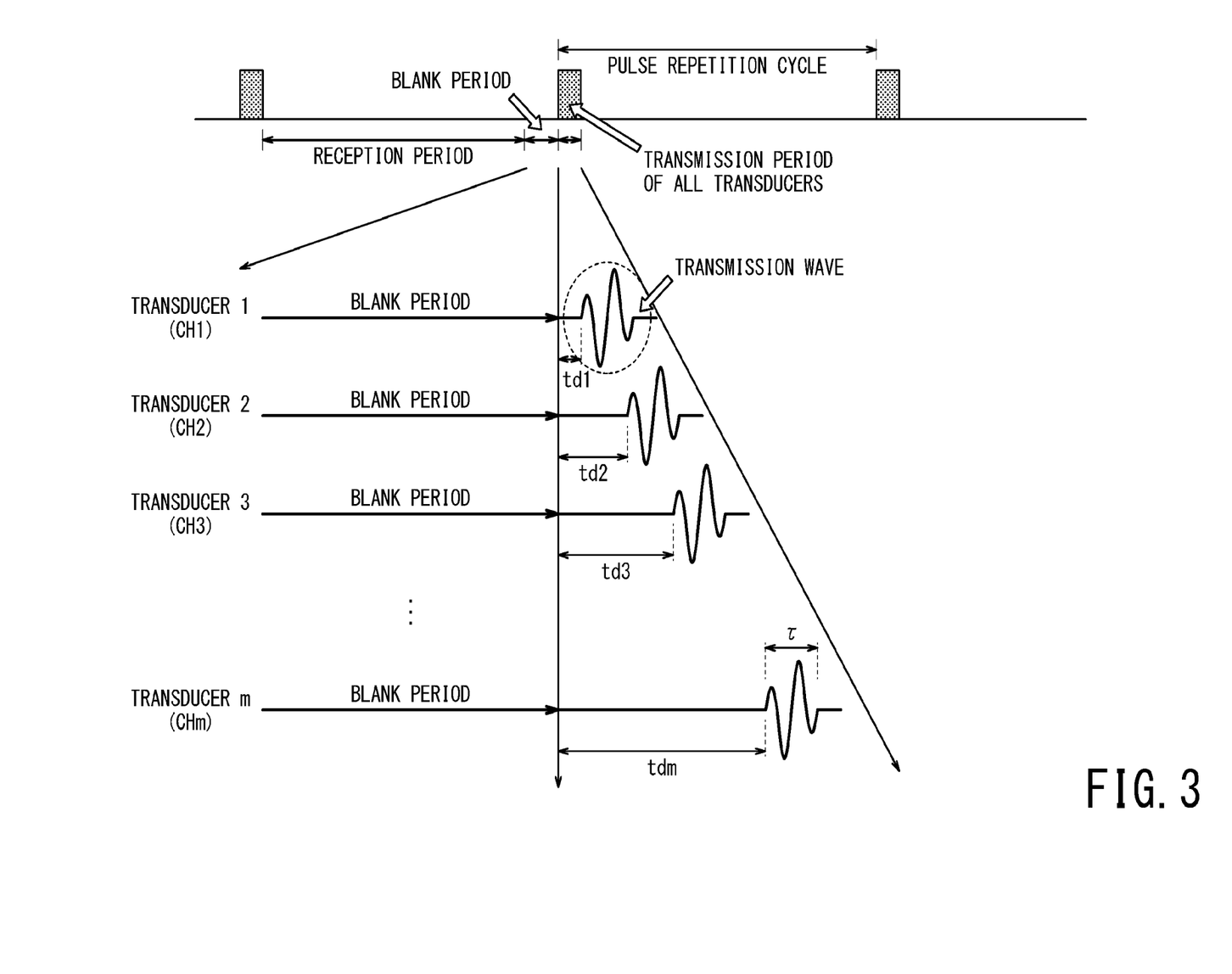
FIG. 3 is a schematic timing chart illustrating timing relationship between respective transmission waves transmitted from transmission-wave generation circuits.

FIG. 3 is a schematic timing chart illustrating timing relationship between the respective transmission waves transmitted from the respective transducers 13 of the ultrasonic probe 10, i.e., between the respective transmission waves separately outputted from the transmission-wave generation circuits 100. As shown in the top part of FIG. 3, a group of transmission waves (i.e., the entirety of the respective transmission waves of all the transducers) are repetitively transmitted in a predetermined cycle. In one cycle, a reception period is set immediately subsequent to a transmission period of a group of transmission waves, and a blank period is set immediately subsequent to this reception period (i.e., between this reception period and the transmission period of a group of transmission waves in the next cycle).

Each of the transmission waves is delayed from a reference position of a signal synchronized with a pulse repetition cycle by a delay time different for each transducer. The reference position is indicated by the arrow vertically extending downward from the center of the top part in FIG. 3. Then, each of the delayed transmission waves are transferred to the respective transducers. In FIG. 3, the delay times for the respective transducers (i.e., channels) are indicated as td1, td2, td3, . . . , tdm. These delay times are determined in accordance with a scanning direction of a transmission beam and a focal-point position of the transmission beam, and are accordingly different for each transducer. Thus, positions of the transmission waves outputted from the respective channels are different from each other. Each transmission wave is a transmission pulse having predetermined pulse length τ. Parameters such as pulse length τ related to a waveform of each transmission wave are generally common to all the channels, although the parameters may change depending on an operation mode.

The delay times for the respective channels are calculated by the setting control circuit 203 of the transmitting circuit 30 on the basis of, e.g., a focal-point position and a scanning direction of a transmission beam supplied from the scan control circuit 50. Additionally or alternatively, the scan control circuit 50 may calculate the delay times of the respective channels based on a focal-point position and a scanning direction of a transmission beam such that the calculated delay times are received by the setting control circuit 203.

The setting control circuit 203 transmits each of the calculated (or received) delay times to the setting circuit 104 of each of the transmission-wave generation circuits 100. Each of the setting circuits 104 temporarily holds the received delay time. Additionally, the parameters related to a waveform of each transmission wave are also transmitted from the setting control circuit 203 to the respective setting circuits 104, and each of the setting circuit 104 holds the received parameters.

The respective waveform generation circuits 103 are arranged at the subsequent stage of the setting circuits 104. Each of the waveform generation circuits 103 generates a transmission wave delayed from the reference position as a digital value, on the basis of the parameters related to a waveform of each transmission wave and the delay time held by the setting circuit 104. The transmission wave (digital value) is generated in real time on the basis of a waveform generation clock outputted from the clock control circuit 202.

The respective DACs 102 are arranged at the subsequent stage of the waveform generation circuits 103. Each of the DACs 102 converts the transmission wave (digital value) generated by the waveform generation circuit 103 into a transmission wave of an analog waveform. This conversion is also performed in real time on the basis of the waveform generation clock outputted from the clock control circuit 202.

The respective transmission amplifiers 101 are arranged at the subsequent stage of the DACs 102. Each of the transmission amplifiers 101 amplifies the transmission wave of an analog waveform converted by the DAC 102 to a predetermined voltage. The amplified transmission waves are transferred to the respective transducers 13 to be transmitted from the ultrasonic probe 10 to an object.

One of the characteristic of the ultrasonic diagnostic apparatus 1 of the present embodiment lies in that each of the transmission waves generated by the respective transmission-wave generation circuits 100 are independently and dynamically controlled at a timing different for each channel. As described above, delay times of respective transmission waves are different between the respective channels depending on a scanning direction and a focus position. In other words, transmission times of the respective transmission waves are different for each channel.

Figure 4:
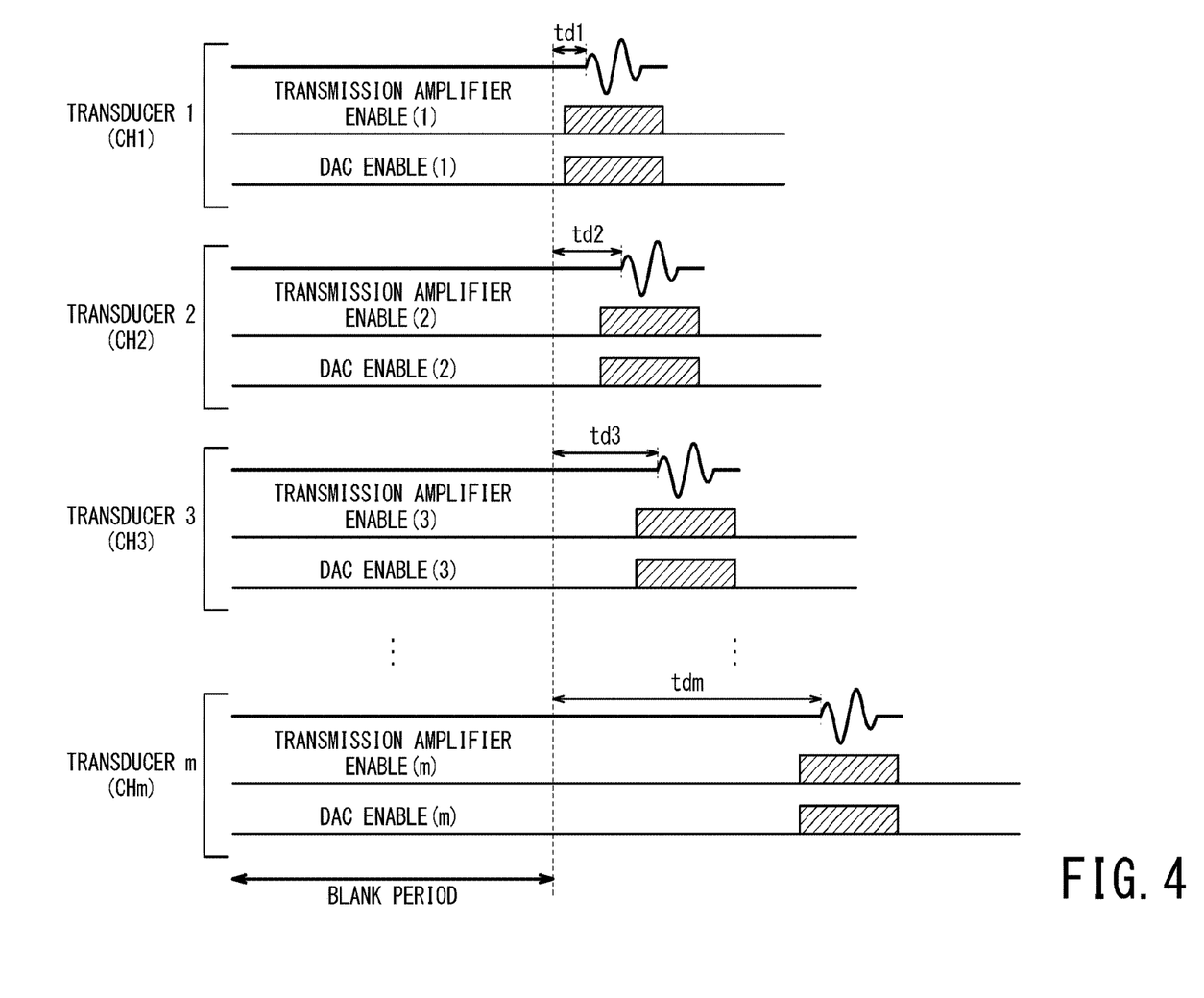
FIG. 4 is a timing chart illustrating a case where an enable period of each transmission amplifier and an enable period of each DAC are adapted to a delay time different for each channel and independently and dynamically controlled at a timing different for each channel.
Figure 5:
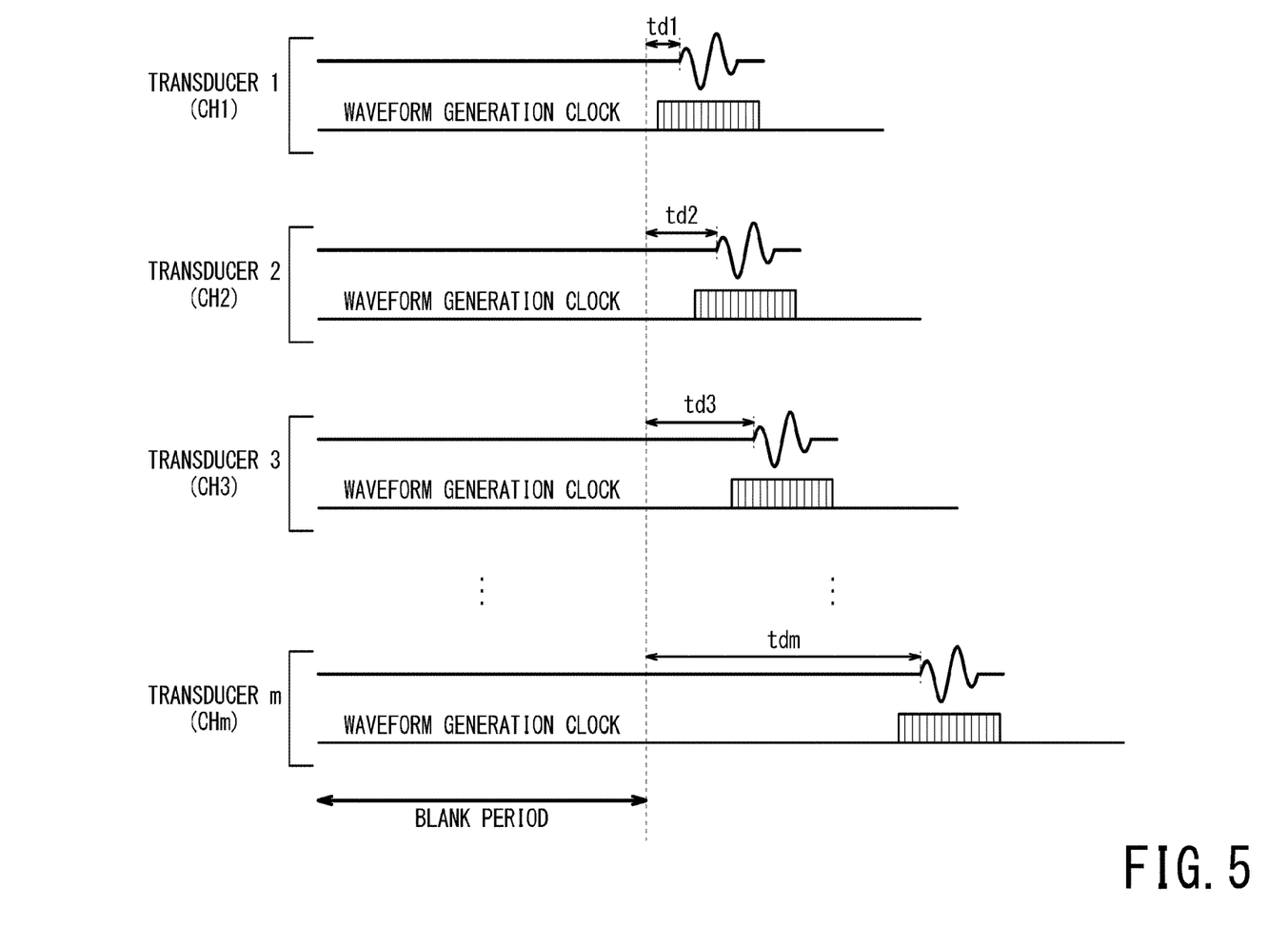
FIG. 5 is a timing chart illustrating a case where each distribution period of the waveform generation clock for generating transmission waves is adapted to a delay time different for each channel and independently and dynamically controlled for each channel.

For this reason, as shown in FIG. 4 and FIG. 5, the ultrasonic diagnostic apparatus 1 of the present embodiment independently and dynamically controls each of the components of each of the transmission-wave generation circuits 100 at a timing different for each channel such that each of transmission waves is generated by being adapted to a delay time different for each channel.

FIG. 4 is a timing chart illustrating a case where an enable period of each transmission amplifier 101 and an enable period of each DAC 102 are adapted to a delay time different for each channel, and independently and dynamically controlled at a timing different for each channel.

In the timing chart of FIG. 4, each of the hatched regions corresponds to an enable period of the transmission amplifier 101 and the DAC 102. The enable period of each channel substantially matches the transmission period of the transmission wave of this channel (i.e., pulse length of the transmission wave), but slightly longer than this pulse length in that the enable period includes predetermined margins immediately before and immediately after the transmission period. That is, the transmission amplifier 101 and the DAC 102 are enabled in each channel only in the period necessary for generating and amplifying the transmission wave.

In other words, the transmission control circuit 200 controls and sets a start timing and an end timing of each enable period of each transmission amplifier 101 in such a manner that each enable period of each transmission amplifier 101 starts immediately before a front end of one transmission pulse and ends immediately after a rear end of this transmission pulse.

Similarly, the transmission control circuit 200 controls and sets a start timing and an end timing of each enable period of each DAC 102 in such a manner that each enable period of each DAC 102 starts immediately before a front end of one transmission pulse and ends immediately after a rear end of this transmission pulse.

In the period during which a transmission amplifier 101 is not enabled (i.e., in its disable period), power consumption of the transmission amplifier 101 is significantly reduced than that in the enable period. Similarly, in the period during which a DAC 102 is not enabled (i.e., in its disable period), power consumption of the DAC 102 is significantly reduced than that in the enable period.

A period during which a transmission amplifier 101 is enabled (i.e., enable period) means such a period that an inputted transmission wave can immediately be amplified and outputted when this transmission wave is inputted to this transmission amplifier 101. A period other than the enable period corresponds to a disable period. During the disable period of the transmission amplifier 101, even when the transmission wave is input to the transmission amplifier 101, the transmission amplifier 101 neither amplifies nor outputs the transmission wave.

Similarly, a period during which a DAC 102 is enabled (i.e., enable period) means such a period that a digital signal can immediately be converted into an analog signal and outputted when digital data are inputted to the DAC 102. A period other than the enable period of the DAC 102 corresponds to a disable period of the DAC 102. During the disable period of the DAC 102, even when a digital signal is inputted to this DAC 102, digital-to-analog conversion is not performed.

FIG. 5 is a timing chart illustrating a case where each distribution period of the waveform generation clock for generating transmission waves is adapted to a delay time different for each channel, and independently and dynamically controlled for each channel. In the timing chart of FIG. 5, each of the vertical-line hatched regions corresponds to a distribution period of each waveform generation clock. Also in FIG. 5, the distribution period of each channel substantially matches the transmission period of the transmission wave of this channel, but slightly longer than this transmission period in that the distribution period includes predetermined margins immediately before and immediately after this transmission period. In other words, the waveform generation clocks (i.e., clock signals or clock pulses) are distributed in the respective channels only in the period necessary for generating each transmission wave. Accordingly, waveform generation clocks distributed to the respective transmission-wave generation circuits 100 are dispersed for each channel, and thus, noise caused by the respective waveform generation clocks is reduced. Additionally, power consumption of the circuit generating the waveform generation clocks is reduced.

Figure 6:
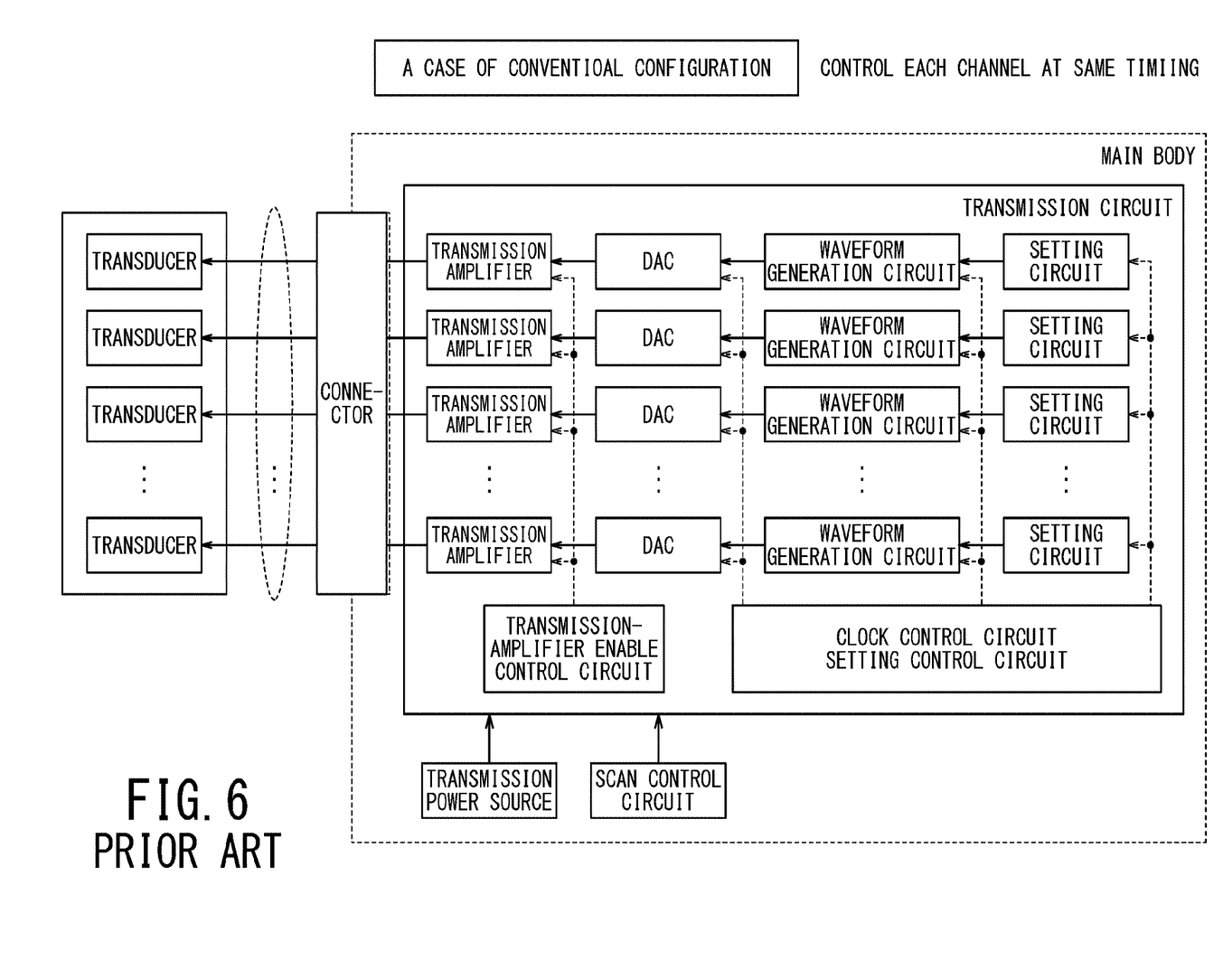
FIG. 6 is a block diagram illustrating configuration of a conventional transmission circuit.

FIG. 6 is a block diagram illustrating configuration of a conventional transmission circuit in comparison with the ultrasonic diagnostic apparatus 1 of the present embodiment. In the conventional transmission circuit as shown in FIG. 6, control for the respective channels is not performed independently but performed in common. For instance, a control signal for enabling is distributed to transmission amplifiers of the respective channels from a transmission-amplifier enable control circuit at a timing common to all the channels (i.e., the same control signal is distributed via the same control line). Similarly, a control signal (e.g., an enable signal) is distributed to digital-to-analog converters (DACs) of the respective channels at a timing common to all the channels (i.e., the same control signal is distributed via the same control line). Additionally, a waveform generation clock is distributed to the waveform generation circuits and setting circuits of the respective channels such that the timing of the waveform generation clock such as its rising edge is common to all the channels.

Figure 7:
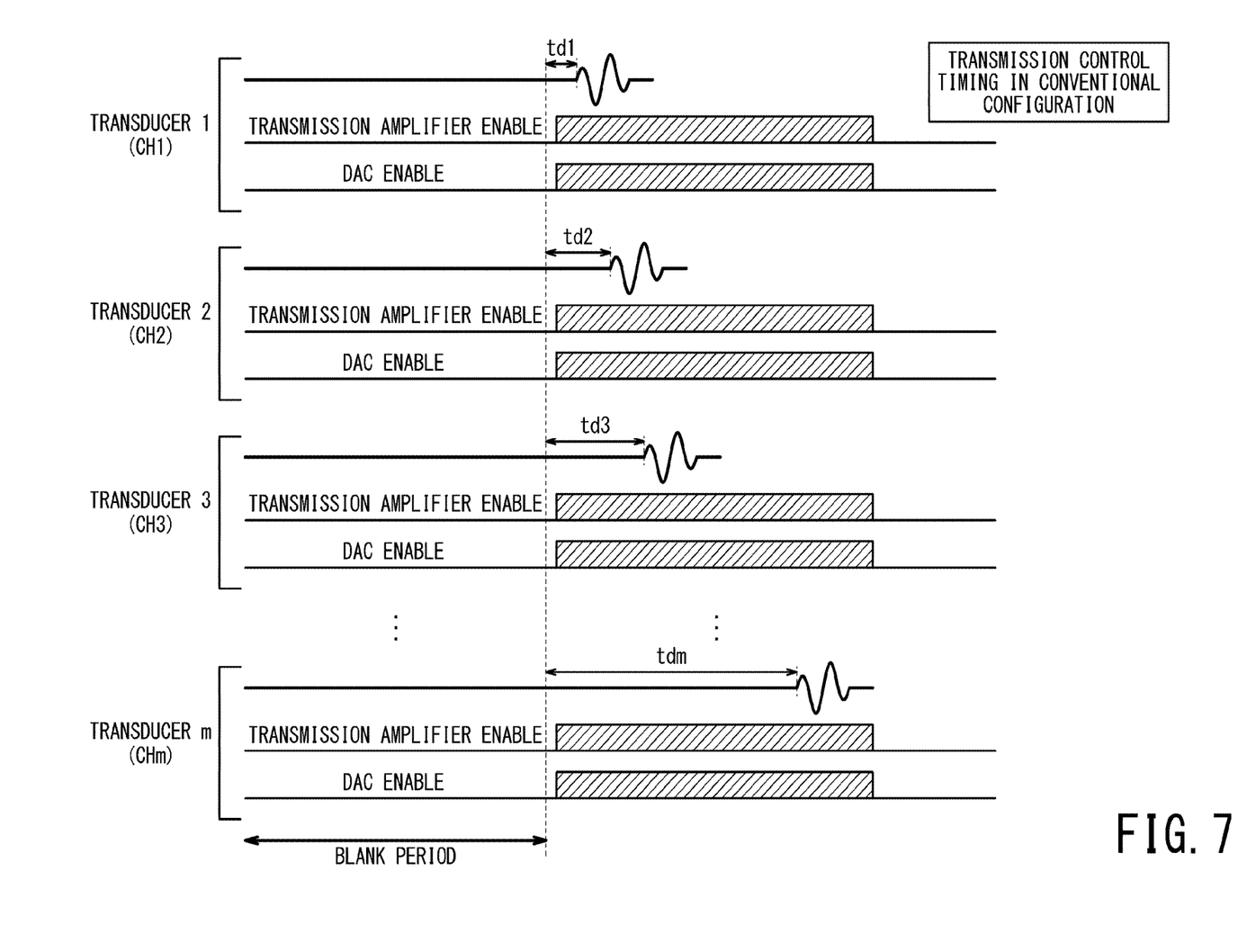
FIG. 7 is a timing chart illustrating an enable period of each transmission amplifier and a timing of an enable period of each DAC in the conventional transmission circuit.

FIG. 7 is a timing chart illustrating an enable period of each transmission amplifier and a timing of an enable period of each DAC in the conventional transmission circuit. In FIG. 7, respective enable periods of the transmission amplifiers and DAC are depicted with hatched regions. As described above, in the conventional transmission circuit, the signal for controlling an enable period of each transmission amplifier and an enable periods of each DAC is common to all the channels. Thus, even though a transmission timing of a transmission wave is different between respective channels, it is unavoidable to set the temporal range covering all the delay times as the enable period which is common to all the transmission amplifiers and all the DACs. In other words, the enable period in the conventional configuration is set so as to temporally cover from the transmission wave having the shortest delay time to the transmission wave having the longest delay time. Thus, power consumption of each of the transmission amplifiers and each of the DAC increases.

Figure 8:
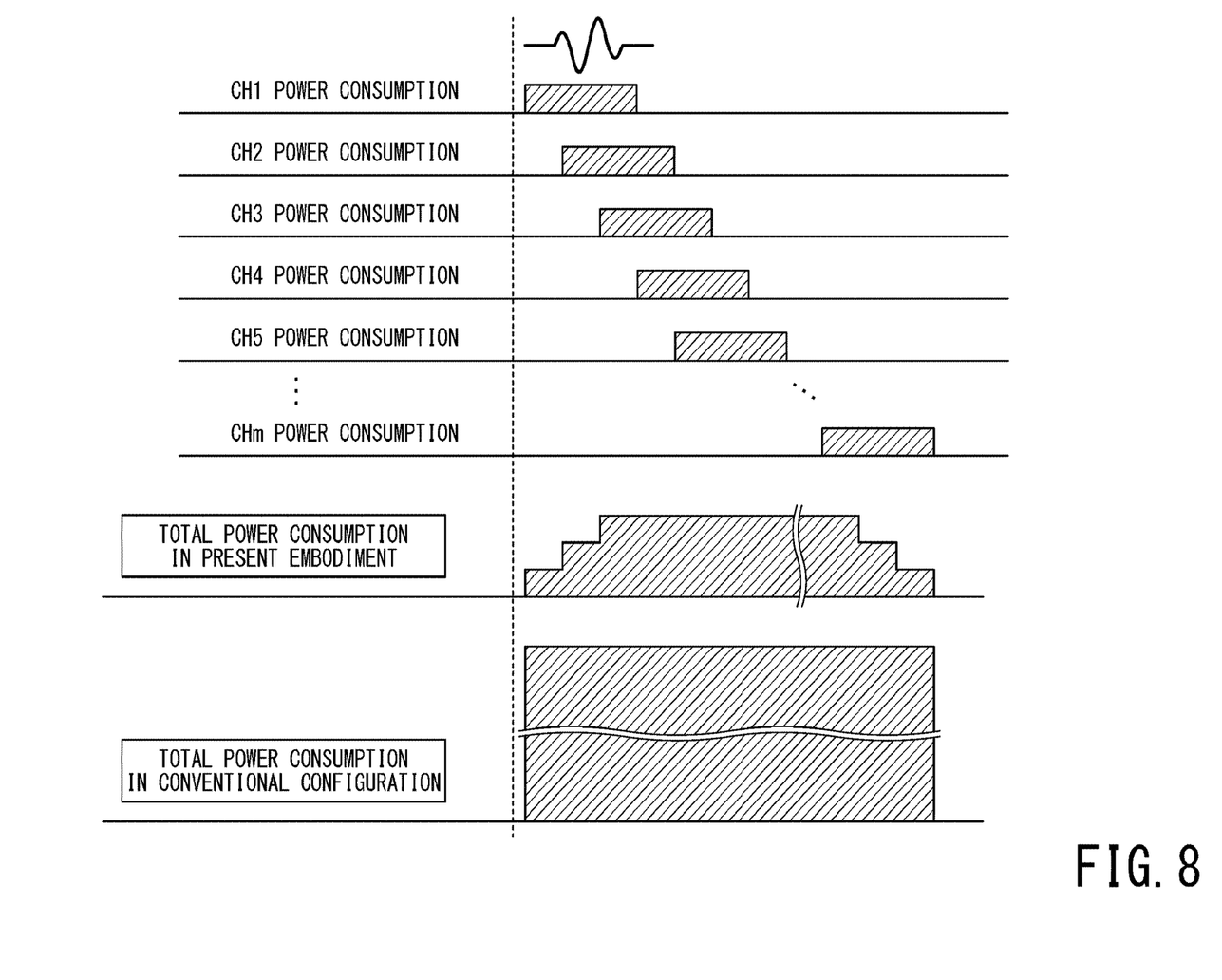
FIG. 8 is a schematic chart conceptually illustrating difference in power consumption between the transmitting circuit of the present embodiment and the conventional transmission circuit.

FIG. 8 is a schematic chart conceptually illustrating difference in power consumption between the transmitting circuit 30 of the present embodiment and the conventional transmission circuit.

The transmitting circuit 30 of the present embodiment independently and dynamically controls enable periods of the respective amplifiers 101 and the respective DACs 102 depending on delay times of the respective channels as described above (FIG. 4). Thus, the total power consumption of the transmission amplifiers 101 and the DACs 102 is dispersed as a result of difference in delay time between the respective channels. In other words, as shown in the second bottom part of FIG. 8, the maximum value of the total power consumption of all the channels is only the total power consumption of channels whose enable periods overlap with each other (in the case of FIG. 8, the total power consumption of three channels).

By contrast, in the conventional transmission circuit, as shown in FIG. 7, the enable period is set as the temporal range which covers all the transmission waves including the transmission wave having the shortest delay time and the transmission wave having the longest delay time. Thus, as shown in the bottom part of FIG. 8, the maximum power consumption of the conventional transmission circuit is the total power consumption of all the channels. Furthermore, this maximum power is required to be continuously supplied from the transmission period of the transmission wave having the shortest delay time to the transmission period of the transmission wave having the longest delay time.

According to the ultrasonic diagnostic apparatus 1 of the present embodiment as described above, power consumption of the transmitting circuit 30 can be reduced by independently and dynamically controlling the respective transmission-wave generation circuits 100 at a timing different for each channel. For instance, power consumption of the transmitting circuit 30 can be reduced by independently and dynamically controlling enable periods of the respective transmission amplifiers 101 and the respective DACs 102 in accordance with delay times different for each channel.

Additionally, the ultrasonic diagnostic apparatus 1 of the present embodiment can reduce occurrence of noise attributable to the waveform generation clock for generating transmission waves, by independently and dynamically supplying respective waveform generation clock signals to the transmission-wave generation circuits of the respective channels at a timing different for each channel in accordance with delay times different for each channel.

Further, according to the ultrasonic diagnostic apparatus 1 of the present embodiment, power consumption of the transmitting circuit 30 can be controlled depending on number of transducers of the ultrasonic probe 10 connected to the main body 20. For instance, consider a case where channel number (i.e., number of the transmission-wave generation circuits 100) of the transmitting circuit 30 is N and number of transducers of the ultrasonic probe 10 connected to the main body 20 is (N-64). The number of transducers of the ultrasonic probe 10 can be determined by, e.g., causing the main body 20 to acquire identification information (ID) of the connected ultrasonic probe 10 via the connector 12.

In this case, the ultrasonic diagnostic apparatus 1 of the present embodiment can control the transmitting circuit 30 for each channel. Thus, power consumption of the transmitting circuit 30 can be suppressed to the minimum level by disabling (i.e., stopping signal transmission to) the transmission amplifier 101 and the DAC 102 of each of the 64 transmission-wave generation circuits 100 of the respective 64 channels which are unnecessary for the connected ultrasonic probe 10. Additionally or alternatively, power consumption of the transmitting circuit 30 can be suppressed to the minimum level by stopping distribution of the waveform generation clocks, data, and setting clocks to the respective transmission-wave generation circuits 100 of the 64 channels in addition to stopping the above signal transmission.

In particular, a two-dimensional array probe is significantly larger in number of transducers than a one-dimensional array probe, which increases channel number of a two dimensional array probe resulting in increase in power consumption. The ultrasonic diagnostic apparatus 1 of the present embodiment can be applied to a two-dimensional array probe, and can reduce noise and power consumption not only at the time of using a one-dimensional array probe but also at the time of using a two-dimensional array probe.

Second Embodiment

Figure 9:
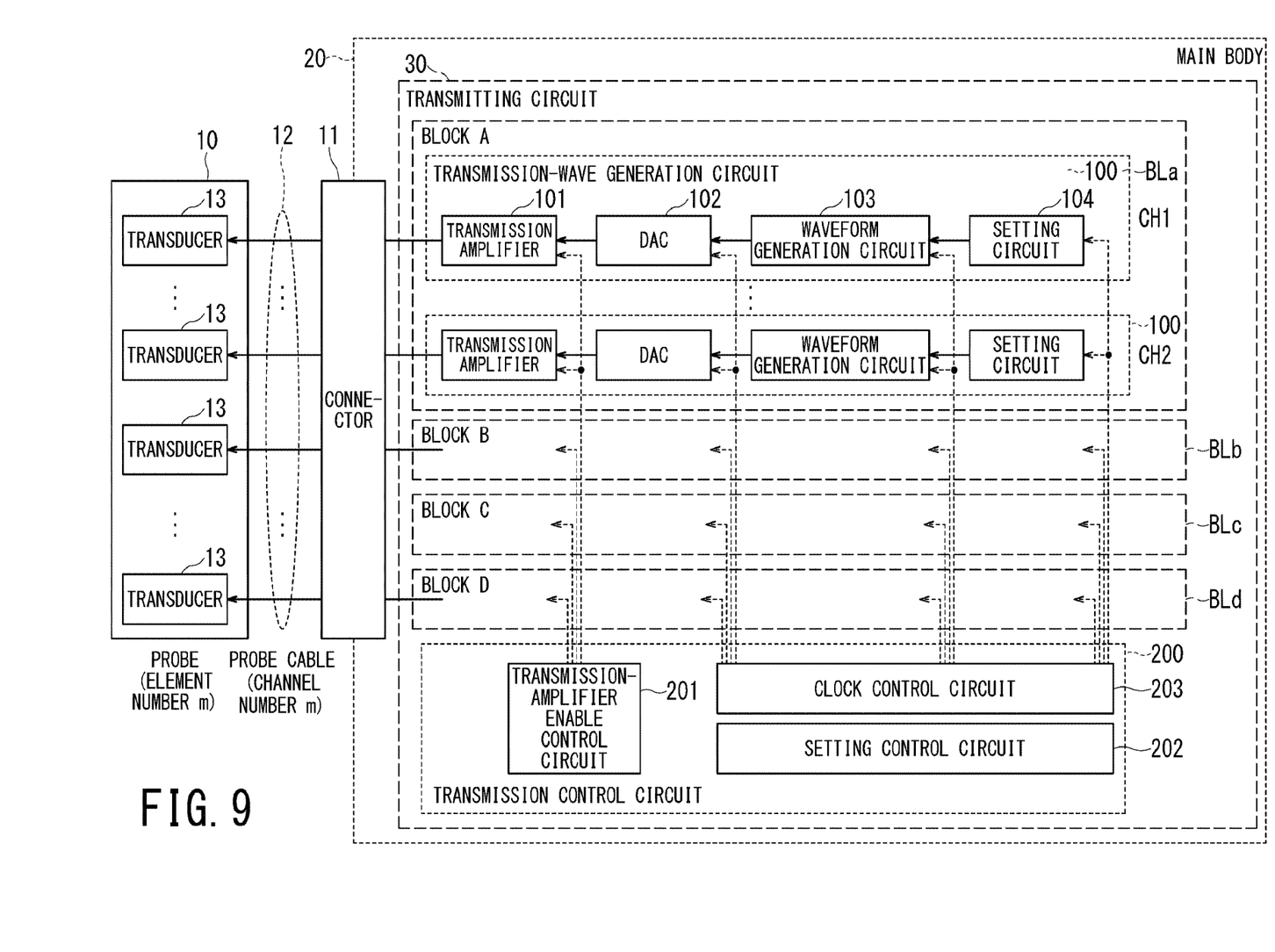
FIG. 9 is a block diagram illustrating detailed configuration of the transmitting circuit of the second embodiment.

FIG. 9 is a block diagram illustrating detailed configuration of the transmitting circuit 30 of the second embodiment. The transmitting circuit 30 of the second embodiment is further configured to be able to control data setting timing for each block in addition to configuration of the first embodiment. Data setting is mainly performed by the setting control circuit 203.

Enable control of the respective transmission amplifiers 101 is independently performed for each channel by the transmission-amplifier enable control circuit 201 in the second embodiment similarly to the first embodiment (FIG. 2). Additionally, enable control of the respective DACs 102 and distribution of the waveform generation clock to the respective channels are independently performed for each channel by the clock control circuit 202 in the second embodiment similarly to the first embodiment. These control lines are, however, omitted to avoid complication in FIG. 9.

Data to be set by the setting control circuit 203 are parameters related to a transmission wave such as a delay time and transmission pulse length. In the second embodiment, these data are independently set at a timing different for each block. Additionally, the setting control circuit 203 controls phases of setting clocks used for data setting in such a manner that the phases are different for each block.

Figure 10:
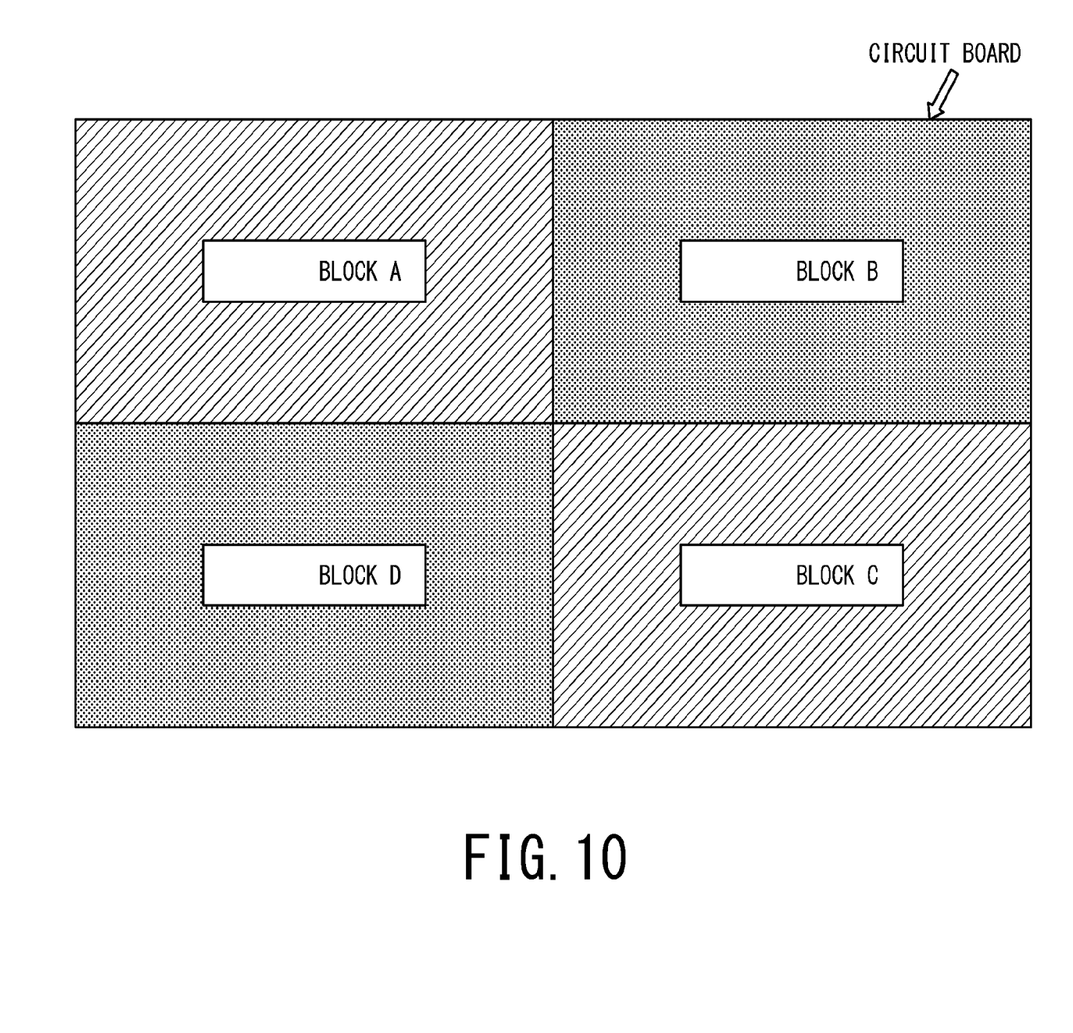
FIG. 10 is a schematic diagram illustrating a concept of block in the second embodiment.

FIG. 10 is a schematic diagram illustrating a concept of "block". The term "block" used in the present specification means a spatially divided region obtained by dividing a printed board by a predetermined number as shown in FIG. 10. In the case of FIG. 10, one printed board is divided into four blocks including a block A to a block D. Out of these four blocks, the block A and the block C are symmetrically arranged about the center point of the printed board, and are not adjacent to each other. Hereinafter, the block A and the block C are collectively referred to as the first block group. Similarly, the block B and the block D are symmetrically arranged about the center point of the printed board, and are not adjacent to each other. Hereinafter, the block B and the block D are collectively referred to as the second block group. In other words, all the predetermined number of blocks are divided into two groups in such a manner that all the blocks of any group are not adjacent to each other (i.e., each group consists of blocks which are not adjacent to each other), one of the two groups is referred to as the first block group, and the other group is referred to as the second block group.

One or plural transmission-wave generation circuits 100, which correspond to predetermined number of channels, is configured, for example, as one integrated circuit (e.g., a Field Programmable Gate Array (FPGA)). In this manner, for instance, plural integrated circuits are grouped into, e.g., four blocks. Then, each block of the integrated circuits is mounted on the printed board separately.

Figure 11:
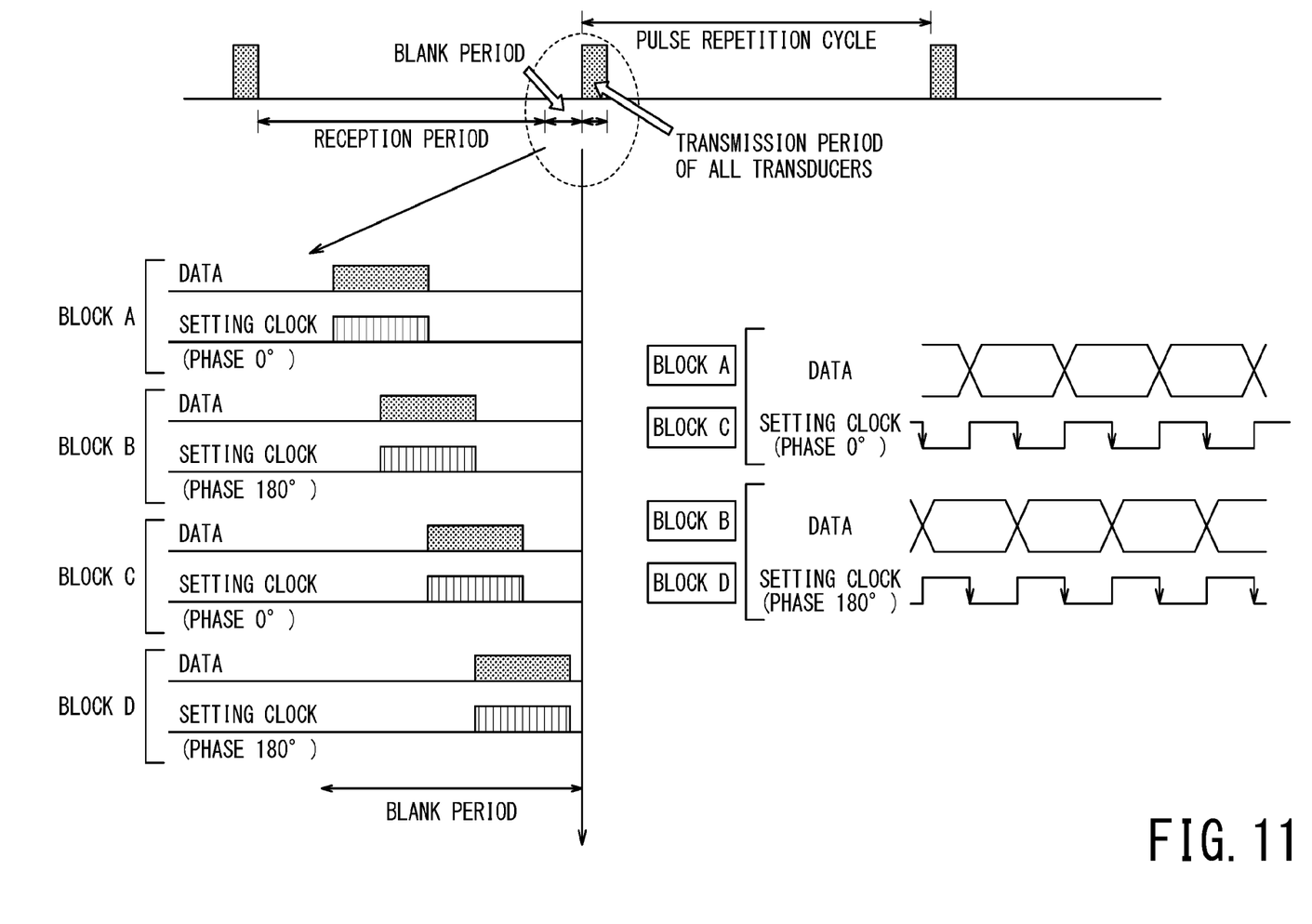
FIG. 11 is a timing chart illustrating a concept of each timing of data setting in the second embodiment.

In the block diagram of FIG. 9, each of the transmission-wave generation circuits 100 of the respective channels CH1 to CHm are grouped into the four blocks, block A (BLa) to block D (BLd). Block A to block D are assigned to each of four segmentations of the printed board, as shown in FIG. 10. FIG. 11 is a timing chart illustrating a concept of each timing of data setting in the second embodiment. As shown in FIG. 11, data are independently set at a timing different for each block. With respect to contents of data, some data, such as delay time, may be different for each channel, or some data such as pulse length, may be common to all the channels.

Data setting is performed in a blank period during which neither transmission nor reception is performed. In data setting, the timing to be set for each block by the setting control circuit 203 is different for each block as shown in FIG. 11 (e.g., the timing to be set for each block is shifted in order). As a result, transmission periods of data and setting clocks are dispersed between blocks, and noise caused by the data and the setting clocks can be reduced.

Moreover, in the second embodiment, the phases of the respective setting clocks are different for each block as shown in the lower right part of the timing chart of FIG. 11, which further reduces noise.

For instance, data are set for the respective transmission-wave generation circuits 100 included in the first block group (i.e., the block A and the block C) by using the setting clock whose phase is zero degree. On the other hand, data are set for the respective transmission-wave generation circuits 100 included in the second block group (i.e., the block B and the block D) by using the setting clock whose phase is 180 degrees. For instance, the block A is adjacent to the blocks B and C as shown in FIG. 10. In this case, clocks whose phases are different from each other are used for the respective blocks adjacent to each other. That is, the phase of the clocks used for block A is different from the phase of the clocks used for blocks B and D. When clocks of the same phase (e.g., clocks which rise at the same timing) are used for respective blocks adjacent to each other, there is a possibility that noise caused by those clocks is increased. However, in the second embodiment, noise caused by the clocks can be reduced, because clocks whose phases are different from each other are used for the respective blocks adjacent to each other.

Meanwhile, since the blocks A and C are not adjacent to each other and spatially separated from each other, possibility of increasing noise is low even if clocks of the same phase are used for the respective blocks A and C.

Note that the number of the block is not limited to four in the above case, but may be other plural number such as 8 and 16. Also in the case of other block number, it is preferable that clocks whose phases are different from each other are used for respective blocks adjacent to each other.

Additionally, phases of respective clocks are not limited to two types of 0 degree and 180 degree. For instance, a setting clock capable of generating four types of clocks whose phases are 0 degree, 90 degrees, 180 degrees, and 270 degrees can be used.

According to the ultrasonic diagnostic apparatus 1 of at least one of the above-described embodiment, power consumption and noise generated from a transmission circuit can be reduced.

Although a description has been given of a case where the ultrasonic diagnostic apparatus 1 of each embodiment is configured to be equipped with the ultrasonic probe 10 so far, embodiments of the present disclosure are not limited to such an aspect. For instance, the ultrasonic diagnostic apparatus 1 may be unequipped with the ultrasonic probe 10 and be capable of being connected to the ultrasonic probe 10. In other words, the main body 20 in FIG. 1 may be treated as the ultrasonic diagnostic apparatus 1 of embodiments.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
   a plurality of transmission-wave generation circuits configured to supply a plurality of transducers of an ultrasonic probe with a plurality of transmission pulses for driving the plurality of transducers via a plurality of channels; and
   a transmission control circuit configured to independently and dynamically control each of the plurality of transmission-wave generation circuits, wherein
   the transmission control circuit is further configured to
     calculate delay times for the respective plurality of channels based on at least one of a focal-point position and a scanning direction of a transmission beam, and
     independently and dynamically control a plurality of enable periods of respective electronic devices in such a manner that
       (a) each of the plurality of enable periods starts immediately before a front end of each of the plurality of transmission pulses and ends immediately after a rear end of each of the plurality transmission pulses,
       (b) a duration of each of the plurality of enable periods becomes substantially same as a pulse width of each of the plurality of transmission pulses, and
       (c) a start time of each of the plurality of enable periods is staggered according to each of the calculated delay times for respective channels of the plurality of channels,
   wherein each of the electronic devices is included in each of the plurality of transmission-wave generation circuits that supply the ultrasonic probe with the plurality of transmission pulses.

2. The ultrasonic diagnostic apparatus according to claim 1,
   wherein the electronic device includes at least one of (a) a transmission amplifier configured to amplify the plurality of transmission pulses, (b) a digital-to-analog converter configured to generate an analog waveform from a digital signal, the analog waveform being inputted to the transmission amplifier, and (c) a circuit configured to supply the plurality of transmission-wave generation circuits with respective waveform generation clocks for generating respective transmission pulses of the plurality of transmission pulses.

3. The ultrasonic diagnostic apparatus according to claim 2,
   wherein the respective transmission pulses are transmission pulses which have delay times different from each other and a predetermined pulse length common to each other; and
   the transmission control circuit is configured to set a start timing and an end timing of each of the enable periods of respective transmission amplifiers, which include the transmission amplifier, for each of the transmission pulses in such a manner that each of the enable periods starts immediately before a front end of one of the transmission pulses and ends immediately after a rear end of the one of the transmission pulses.

4. The ultrasonic diagnostic apparatus according to claim 2,
   wherein the respective transmission pulses are transmission pulses which have delay times different from each other and a predetermined pulse length common to each other; and
   the transmission control circuit is configured to set a start timing and an end timing of each of the enable periods of respective digital-to-analog converters, which include the digital-to-analog converter, for each of the transmission pulses in such a manner that each of the enable periods of the respective digital-to-analog converters starts immediately before a front end of one of the transmission pulses and ends immediately after a rear end of the one of the transmission pulses.

5. The ultrasonic diagnostic apparatus according to claim 1, wherein,
   each of the plurality of transmission-wave generation circuits includes a transmission amplifier and a digital-to-analog converter as the electronic device, and the plurality of transmission-wave generation circuits are grouped into a plurality of blocks; and
   transmission control circuit configured to supply the plurality of transmission-wave generation circuits with respective clocks and respective data with an independent timing different from each of the plurality of blocks-, each of the respective data being for generating a transmission wave and including at least a delay time for each channel.

6. The ultrasonic diagnostic apparatus according to claim 5, wherein the transmission control circuit is configured to supply the plurality of transmission-wave generation circuits with the respective clocks and the respective data in a blank period provided between a reception period and a transmission period.

7. The ultrasonic diagnostic apparatus according to claim 5, wherein
   the plurality of transmission-wave generation circuits are configured to be divided into the plurality of blocks so as to be arranged on a circuit board for each block; and
   the transmission control circuit is configured to set phases of the respective clocks in such a manner that the phases of the respective clocks are different for each block.

8. The ultrasonic diagnostic apparatus according to claim 7, wherein
   the transmission control circuit is configured to
     classify each of the plurality of blocks into a first group or a second group in such a manner that each of the first group and second group consists of blocks which are not adjacent to each other, and set phases of the respective clocks in such a manner that a phase of every block of the first group is different by 180 degrees from a phase of every block of the second group.

* * * * *